(12) United States Patent
Tsukii et al.

(10) Patent No.: US 7,999,929 B2
(45) Date of Patent: Aug. 16, 2011

(54) SPECIMEN OPTICAL INFORMATION RECOGNIZING DEVICE AND ITS RECOGNIZING METHOD

(75) Inventors: Ken Tsukii, Tokyo (JP); Jie Xu, Tokyo (JP); Kenichi Kimura, Tokyo (JP); Satoshi Sugiyama, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 657 days.

(21) Appl. No.: 11/659,132

(22) PCT Filed: Aug. 1, 2005

(86) PCT No.: PCT/JP2005/014057
§ 371 (c)(1),
(2), (4) Date: Feb. 1, 2007

(87) PCT Pub. No.: WO2006/013832
PCT Pub. Date: Feb. 9, 2006

(65) Prior Publication Data
US 2009/0021722 A1    Jan. 22, 2009

(30) Foreign Application Priority Data
Aug. 2, 2004 (JP) .................................. 2004-226155

(51) Int. Cl.
*G01N 21/00* (2006.01)
(52) U.S. Cl. ........................................................ 356/73
(58) Field of Classification Search .......... 356/244–246, 356/72–73; 422/102
See application file for complete search history.

(56) References Cited

U.S. PATENT DOCUMENTS

| | | | | |
|---|---|---|---|---|
| 3,573,470 A | * | 4/1971 | Haley | 356/246 |
| 4,818,492 A | * | 4/1989 | Shimizu | 422/100 |
| 4,867,559 A | * | 9/1989 | Bach | 356/73 |
| 5,445,994 A | | 8/1995 | Gilton | |

(Continued)

FOREIGN PATENT DOCUMENTS

JP    51-60282    5/1976

(Continued)

OTHER PUBLICATIONS

Japanese Office Action issued Oct. 15, 2010, in Patent Application No. 2006-531466 (with partial English-language translation).

*Primary Examiner* — Kara E Geisel
(74) *Attorney, Agent, or Firm* — Oblon, Spivak, McClelland, Maier & Neustadt, L.L.P.

(57) ABSTRACT

A specimen optical information recognizing device includes a specimen containing section containing a specimen to be measured, a specimen measuring section having a light source for outputting light for observing the specimen, a photodetecting section for collecting optical information from the specimen, and an optical waveguide for propagating light between the specimen containing and the specimen measuring sections. The optical information on the specimen may be recognized by measuring values under at least two measurement conditions. The specimen optical information recognizing device includes a measurement auxiliary liquid interposed between the end of the optical waveguide and the specimen. A longitudinal cross section of the specimen containing section may be of a recessed shape, and the aperture depth of the recessed portion may be greater than the aperture diameter. A through hole may be provided at least in a part near the bottom of the specimen containing section.

29 Claims, 9 Drawing Sheets

U.S. PATENT DOCUMENTS

| | | | |
|---|---|---|---|
| 5,744,305 A | 4/1998 | Fodor et al. | |
| 6,388,750 B1 * | 5/2002 | Liu et al. | 356/246 |
| 2002/0149773 A1 * | 10/2002 | Martino et al. | 356/436 |
| 2003/0128371 A1 * | 7/2003 | Vaux et al. | 356/237.2 |
| 2003/0142309 A1 * | 7/2003 | Kuebler et al. | 356/338 |
| 2010/0231913 A1 | 9/2010 | Tsukii et al. | |

FOREIGN PATENT DOCUMENTS

| | | |
|---|---|---|
| JP | 5 264447 | 10/1993 |
| JP | 11 64213 | 3/1999 |
| JP | 11 326152 | 11/1999 |
| JP | 2002 257732 | 9/2002 |
| JP | 2002 340909 | 11/2002 |
| JP | 2002 355090 | 12/2002 |
| JP | 2003 329681 | 11/2003 |
| JP | 2004 125748 | 4/2004 |
| WO | 02 063300 | 8/2002 |
| WO | 03 031952 | 4/2003 |

* cited by examiner

FIG. 11A  FIG. 11B  FIG. 11C
liquid housing area
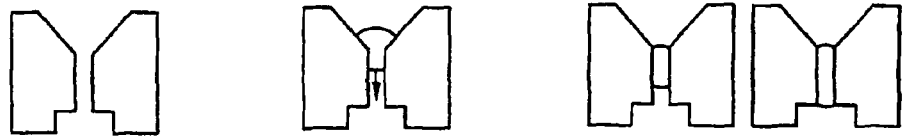
FIG. 12
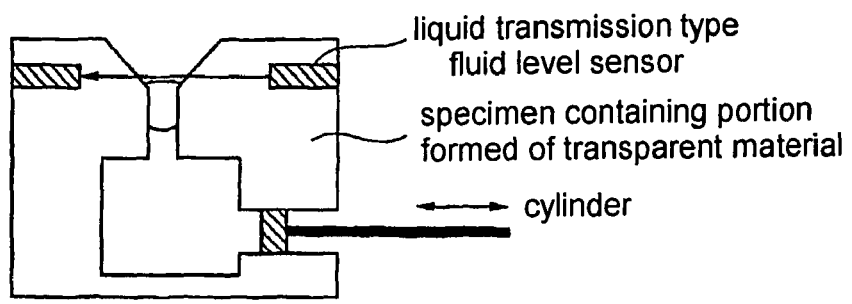
FIG. 13A  FIG. 13B
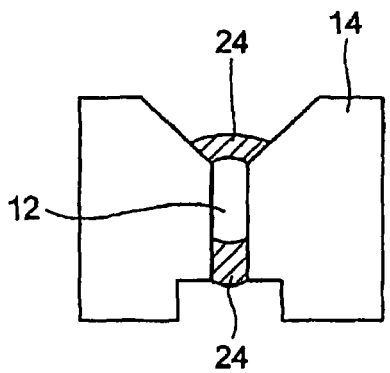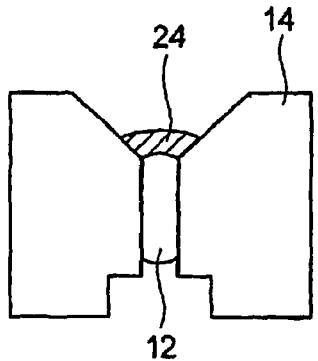

BACKGROUND ART

BACKGROUND ART

SPECIMEN OPTICAL INFORMATION RECOGNIZING DEVICE AND ITS RECOGNIZING METHOD

TECHNICAL FIELD

The present invention relates to apparatus and method for recognizing optical information from a specimen. In particular, the invention relates to various fields in which the investigation and analysis regarding gene, immune system, biomolecule such as protein, amino acid, and saccharide are required, for example engineering field, agricultural science such as food product, agricultural product, and seafood processing, pharmaceutical field, medical science field such as hygienics, health care, immune, epidemic, and gene, science field such as chemistry or biology.

BACKGROUND ART

Researches regarding biomolecule have been carried out for various objects such as clinical examination, making new drugs, and development for environment field and food evaluation field. Apparatuses for analyzing information included in the biomolecule with high sensitivity are becoming more important. FIG. 15 shows a conventional apparatus 101 for recognizing optical information from a specimen. Described below is the conventional apparatus for recognizing optical information from a specimen with reference to FIG. 15.

The conventional apparatus 101 for recognizing optical information from a specimen is composed of a specimen containing portion 105 for containing a specimen 103 to be measured, a specimen measuring portion 111 including a light a light source 107 for outputting a light to observe the specimen 103 and a photodetecting portion 109 for collecting optical information from the specimen, and a light collector 113 for collecting the light output from the light source 107 and transmitted though a space to irradiate the specimen 103 with the light. The specimen containing portion 105 is of a plate reader structure 105a or a chip reader structure 105b as shown in FIG. 16 and FIG. 17.

The plate reader structure 105a is configured so that, as shown in FIG. 16, a plurality of recessed portions is formed in the specimen containing portion 105 at given intervals, and the specimens 103 are contained in the recessed portions. The chip reader structure 105b is configured so that, as shown in FIG. 17, the surface of the specimen containing portion is smoothen, and the specimens 103 are arranged on the smooth surface at given intervals.

[Patent Document 1] U.S. Pat. No. 5,445,994
[Patent Document 2] U.S. Pat. No. 5,744,305
[Patent Document 3] International Publication No. WO 02/063300

DISCLOSURE OF THE INVENTION

Problems to be solved by the Invention

The above-mentioned conventional apparatus for recognizing optical information from a specimen, however, has the following problems. First, problems in the specimen containing portion will be described. When the specimen containing portion is of the above-mentioned chip reader structure, there is a possibility that a sample may evaporate immediately after drop of the sample because the chip reader structure is a plane structure measuring system, resulting in the lower reactivity of the specimen. In addition, the evaporation of the specimen changes the concentration of the specimen and the fluid level of the sample, making it difficult to use the chip reader structure for measuring the progress of the reaction of the specimen in real time.

Further, when the specimen is arranged with high density, there are problems in the measurement sensitivity of the optical information from the specimen. The greater the density of the specimen, the lower the measurement sensitivity. Furthermore, since the photodetecting portion for collecting the optical information from the specimen is fixed to given location, the specimen to be measured should always be positioned at the predetermined same position. Accordingly, if the position is deviated from the predetermined position, the optical information from the specimen decreases, resulting in the lower measurement sensitivity.

On the other hand, since the above-mentioned plate reader structure uses several dozen to several hundred µl of fluid volume per well for the reaction and measurement, there is needs for minimizing an amount of the samples to be used. However, it is likely to cause a problem such as insufficient sensitivity and reaction, and therefore it is difficult to measure minute amount of the sample. Furthermore, like the chip reader, since the photodetecting portion for collecting the optical information from the specimen is fixed to given location, the specimen to be measured should always be positioned at the predetermined same position. Accordingly, if the position is deviated from the predetermined position, the optical information from the specimen decreases, resulting in the lower measurement sensitivity.

Second, problems other than those related to the specimen containing portion will be described. The conventional apparatus for recognizing the optical information from the specimen is configured so that the light output from the light source is transmitted through the air to irradiate the specimen. If the air (airspace) is present between the specimen and the optical measurement system (the light source or photodetecting portion), the optical noise due to Fresnel reflection, or the like is generated upon the propagation of the light, resulting in the lower measurement sensitivity. Moreover, since the specimen is exposed to the air, contaminants may be mixed in the specimen sample after the specimen is housed in the specimen containing portion. In addition, the specimen is irradiated with the light by use of the light concentrating means, therefore, the light concentration position has to be adjusted based on the amount of specimen sample. Accordingly, it is necessary to adjust the position of the light concentrating means. There is a difficulty in this adjustment of the position of the light concentrating means.

The present invention is provided to solve the above-mentioned conventional problems, and an object thereof is to provide an apparatus and method for recognizing optical information from a specimen capable of measuring the specimen with high sensitivity.

Means for solving the Problems

In order to achieve the above-mentioned object, the present invention has the following structures as means to solve the problems.

According to an aspect of the present invention, there is provided an apparatus for recognizing optical information from a specimen, which comprises: a specimen containing portion for containing a specimen to be measured; a specimen measuring portion including a photodetecting portion for collecting optical information from the specimen; and an optical waveguide for transmitting a light between the specimen containing portion and the specimen measuring portion, wherein the optical information from the specimen is recognized based on measurement values measured under two or more measurement conditions.

According to another aspect of the present invention, there is provided an apparatus for recognizing optical information from a specimen, which comprises: a specimen containing portion for containing a specimen to be measured; a specimen measuring portion having a photodetecting portion for collecting optical information from the specimen; an optical waveguide for transmitting a light between the specimen containing portion and the specimen measuring portion; and a measurement auxiliary liquid interposed between a tip of the optical waveguide and the specimen.

According to still another aspect of the present invention, there is provided an apparatus for recognizing optical information from a specimen, which comprises: a specimen containing portion for containing a specimen to be measured, the specimen containing portion having a first surface with which the specimen finally contained therein comes in contact and other surfaces with which the specimen finally contained therein does not come in contact, wherein the first surface has an affinity for the specimen equal to or larger than the other surfaces; a specimen measuring portion comprising a photodetecting portion for collecting optical information from the specimen; and an optical waveguide for transmitting a light between the specimen containing portion and the specimen measuring portion.

According to still another aspect of the present invention, there is provided a specimen measuring system, which comprises: any one of the above-mentioned apparatuses for recognizing optical information from a specimen; a measuring unit for operating the apparatus for recognizing optical information from a specimen and for collecting an information on the specimen; and a controlling and analyzing device for analyzing the information from the measuring unit and for controlling the apparatus for recognizing optical information from a specimen.

Effect of the Invention

According to the present invention, in the apparatus for recognizing optical information from a specimen, the specimen containing portion has a first surface with which the specimen finally contained therein comes in contact and other surfaces with which the specimen finally contained therein does not come in contact, and the first surface has an affinity for the specimen equal to or larger than the other surfaces, making it possible to prevent the specimen from being mixed in fine holes for other samples to thereby prevent the contamination and improve while the containing performance of the specimen is maintained, furthermore prevent specimens from being adhered and agglomerated to a wall surface to improve the reactivity, which enhances reactivity.

Further, according to the present invention, the specimen containing portion has a concave portion in vertical cross-section for containing the specimen, and the opening depth of the concave portion is equal to or larger than the opening diameter. This shape makes it possible to reduce the specimen that does not contribute to the measurement sensitivity of the light at circumference, and reduce the specimen amount drastically while keeping the measurement sensitivity.

Furthermore, the specimen can be easily contained in the specimen containing portion by maintaining the hydrophilicity of the inner wall of the concave portion equal to or larger than other surfaces.

In addition, the similar effects are obtained by forming the specimen containing portion having an air leakage passage such as a through hole.

Specifically, when the specimen containing portion has a through hole, the hole has a diameter of 1.5 mm or less, or a diameter of a value not larger than the dimension thereof. Even in the case of the through hole, by properly selecting hydrophilicity or hydrophobicity of the wall of the through hole in accordance with the shape the through hole, the specimen can be held by the wall or bottom portion of the specimen containing portion without running off due to the surface tension of the specimen itself.

In order to carry out a precise optical measurement, it is important to set a distance between the tip of the waveguide and the specimen, specifically the upper surface of the specimen to be constant. For this purpose, it is necessary to control the position of the upper surface of the specimen.

One way for achieving this control is that an opening at the upper portion of the hole is formed in a cone-shaped. This makes it possible to stabilize the fluid level of the specimen. In other words, when a much amount of the supplied specimen exist in the cone-shaped portion, the specimen goes down in the hole due to the weight of the specimen at this portions, but when a remaining amount of the specimen at the cone-shaped portion decreases gradually, the surface tension of the specimen itself and absorbability to the wall exceed the weight to thereby stop the decent of the specimen, and finally the specimen stands still.

Specifically, when a hole has a diameter of 1.5 mm or less, or a diameter of a value not larger than the dimension thereof, dominant factors in positioning of the upper surface of the specimen are (i) the shape of the specimen containing portion, (ii) the surface property of the specimen containing portion, (iii) the specimen, and (iv) the affinity of the specimen for the surface of the specimen containing portion, and the weight of the specimen less dominant factors to decide the position of the upper surface, and the weight of the specimen less contributes. Accordingly, if the amount of supplied specimen varies, the position of the contained specimen surface can be controlled to be approximately constant.

In addition, as shown in FIG. 10, the opening at the upper portion of the hole is formed in a cone-shape, making it possible to promote supply of the measurement auxiliary liquid. More specifically, even though a simple supply means such as needle is arranged adjacent to the tip of the optical waveguide, the specimen can be sufficiently approached to the tip of the optical waveguide. Furthermore, it is advantageous that the variation in the amount of supplied measurement auxiliary liquid does not cause problems such as the change in the measurement condition and contamination, since the capacity of the cone-shaped portion is large.

In order to control the fluid level of the specimen more accurately, it is preferable that a space below the specimen is sealed and the volume or pressure of this space is changed so as to change the position of the specimen. The use of a sensor for detecting the liquid level enables the accurate fluid level of the specimen.

In this specimen containing portion, a temperature controller for controlling a temperature of the specimen and a vibrator for vibrating the specimen to promote reaction are provided. Therefore, even if a sample quantity of the specimen is a quantity level (nL) which is too small to be agitated by pipetting, agitation can be performed. Furthermore, the specimen can be agitated without using a means for agitating with it comes in contact with the specimen, making it possible to prevent contaminated materials from being mixed in. Moreover, a temperature control suitable for the specimen observation or a temperature control suitable for the agitation and reaction of the specimen can be performed by temperature control of the specimen containing section. Accordingly, an observation measurement can be carried out with the specimen in the optimal conditions (observation temperature, reactions conditions).

Furthermore, according to the present invention, in the specimen containing portion, since the measurement auxiliary liquid is interposed between the tip of the optical waveguide and the specimen, the light irradiates the specimen without transmitting in the air, and the optical information from the specimen is brought to the optical waveguide without passing through the air. Hence, Fresnel reflection can be reduced, making it possible to perform the high sensitivity measurement without making the tip of the optical waveguide come in contact with the specimen. Accordingly, even when a successive observation of specimens can be performed, it is possible to prevent contaminants from being mixed in other specimens. Moreover, since the specimen is sealed by the measurement auxiliary liquid without coming in contact with the air, the evaporation of the specimen can be prevented. In addition, since the tip of the optical waveguide or the tip of the optical waveguide including a portion to which the optical waveguide is fixed is designed to be tapered, even if an amount of specimen sample is smaller, the tip of the optical waveguide can be approached closer to the specimen.

Besides, according to the present invention, since the tip of the optical waveguide or the tip of the optical waveguide including a portion to which the optical waveguide is fixed is designed to be tapered, the outside of the specimen containing portion as well as the internal of the specimen containing portion can be easily scanned.

Thus, wherever the specimen positions in the specimen containing portion (for example, the specimen is not positioned in the center of the specimen containing portion), the specimen can be efficiently irradiated with the light while collecting optimal optical information from the specimen by scanning the specimen with the tip of the optical waveguide. Further, the optical waveguide is designed to be movable to scan the specimen with the tip of the waveguide. As a result, the optical information from the specimen can be obtained at a plurality of locations, for example several locations where distances from the specimen or angles to the specimen are different. Moreover, the optical information from the specimen can be recognized based on measured values measured under two or more measurement conditions such as wavelength and light intensity. Consequently, wherever the specimen positions in the specimen containing position, there is no variation in measurement values and the measurement with high sensitivity and high reproductively can be performed.

Furthermore, since the measurement auxiliary liquid is water-insoluble, it is not mixed in the specimen. As a result, the optical waveguide can be arranged at a position closer to the specimen without interposing the air therebetween, and it is also possible to keep the specimen in the optimal condition without drying the specimen, therefore the specimen can be measured with high sensitivity.

BRIEF DESCRIPTION OF THE DRAWINGS

From FIG. 1A to FIG. 1C are schematic views showing one embodiment of an apparatus for recognizing optical information from a specimen according to the present invention.

From FIG. 2A to FIG. 2D are schematic views showing one embodiment of a specimen containing portion used in the apparatus for recognizing optical information from a specimen according to the present invention.

Figure 3A:
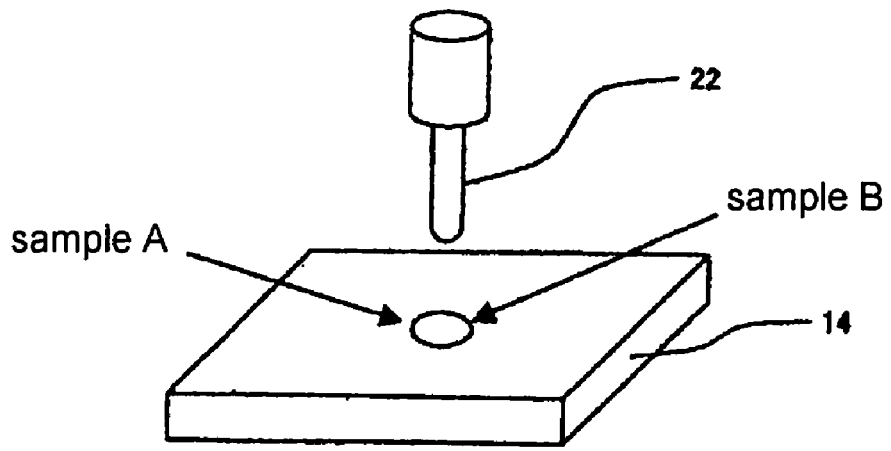
Figure 3B:
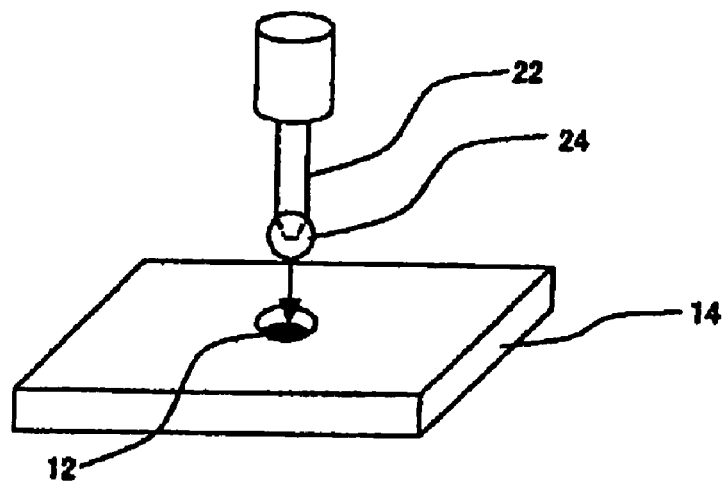
Figure 3C:
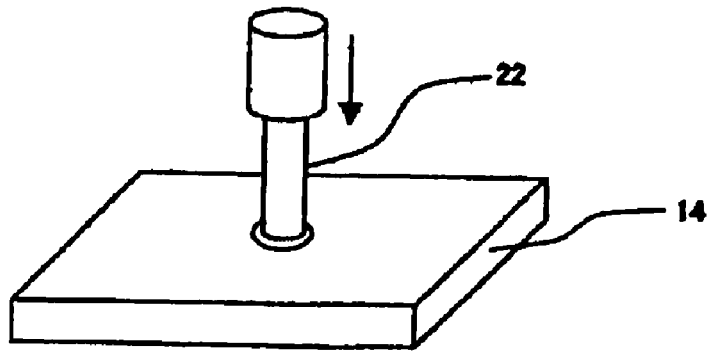

From FIG. 3A to FIG. 3C are schematic views showing one embodiment of an optical waveguide used in the apparatus for recognizing optical information from a specimen according to the present invention.

Figure 4A:
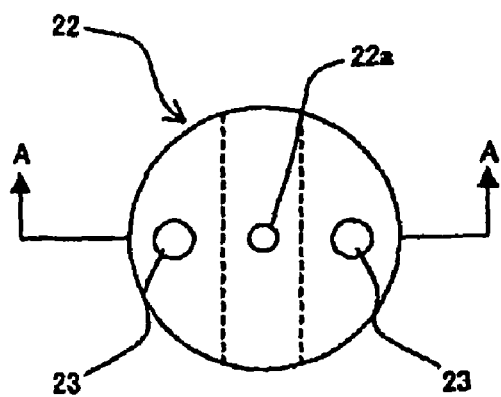
Figure 4B:
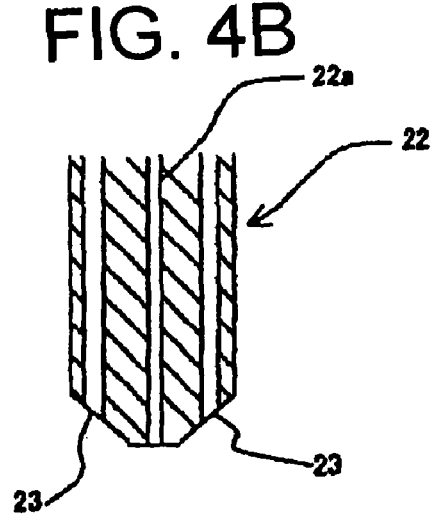

FIG. 4A is a plane view showing one embodiment of a optical waveguide used in the apparatus for recognizing optical information from a specimen according to the present invention, and FIG. 4B is a cross-sectional view along the line A-A of FIG. 4A.

Figure 5:
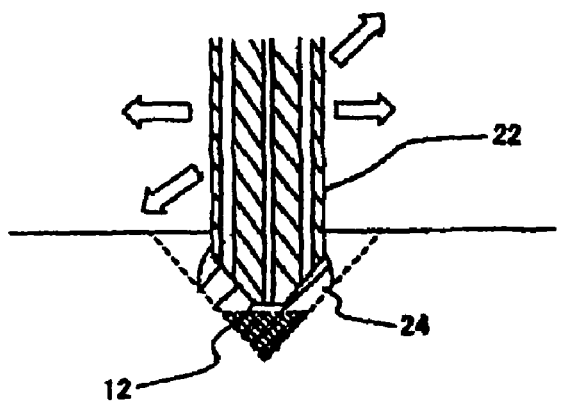

FIG. 5 is a schematic view showing one embodiment of an fiber capable of scan measurement using the optical waveguide in the apparatus for recognizing optical information from a specimen according to the present invention.

Figure 6:
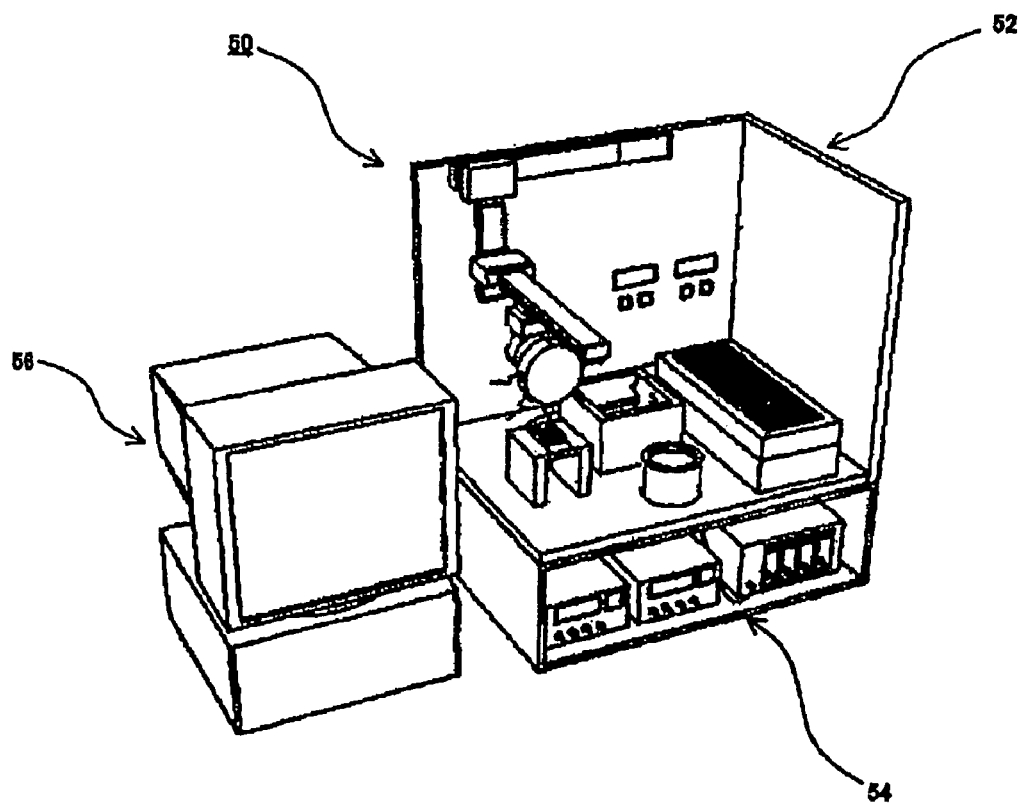

FIG. 6 is a schematic view showing one embodiment of a specimen measuring system according to the present invention.

Figure 7:
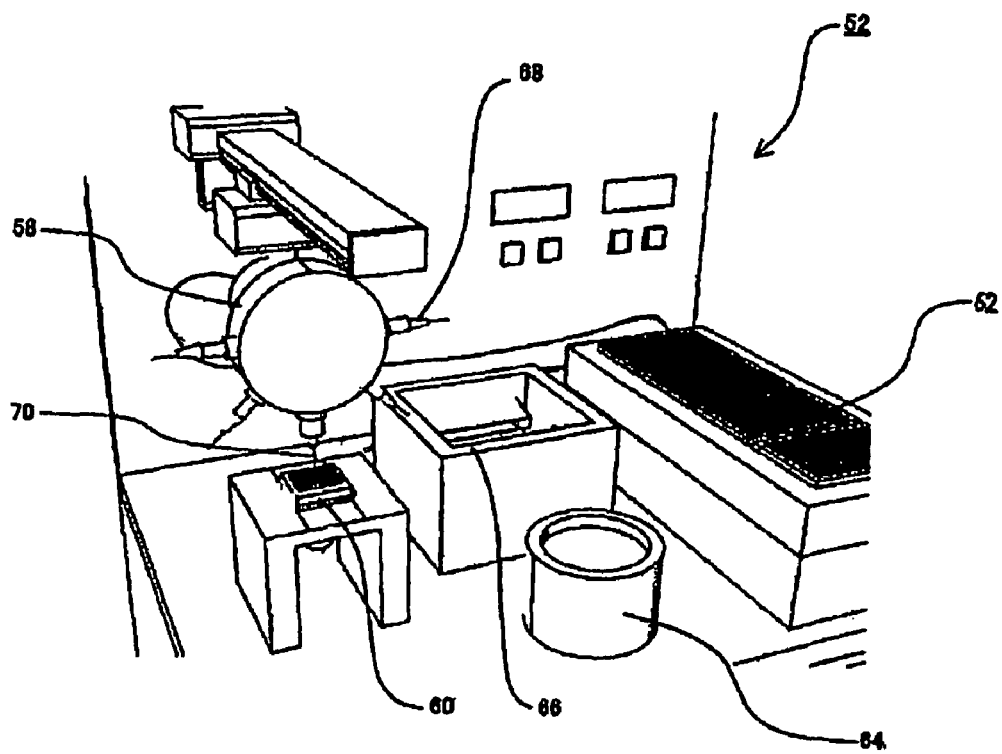

FIG. 7 is a schematic view showing one embodiment of the measuring unit in the specimen measuring system according to the present invention.

Figure 8:
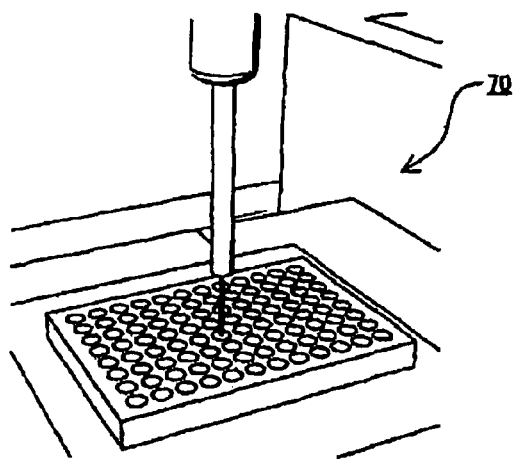

FIG. 8 is a schematic diagram showing one embodiment of a fiber measuring portion of the measuring unit in a specimen measuring system according to the present invention.

Figure 9:
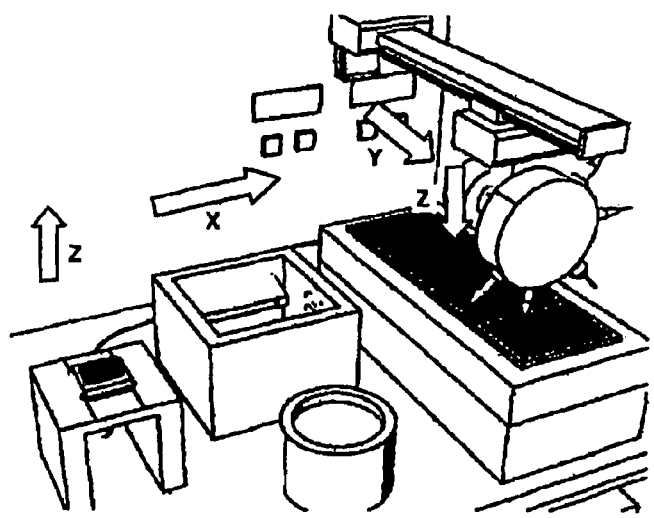

FIG. 9 is an explanatory diagram for explaining a way of taking a sample in a specimen measuring system according to the present invention.

Figure 10:
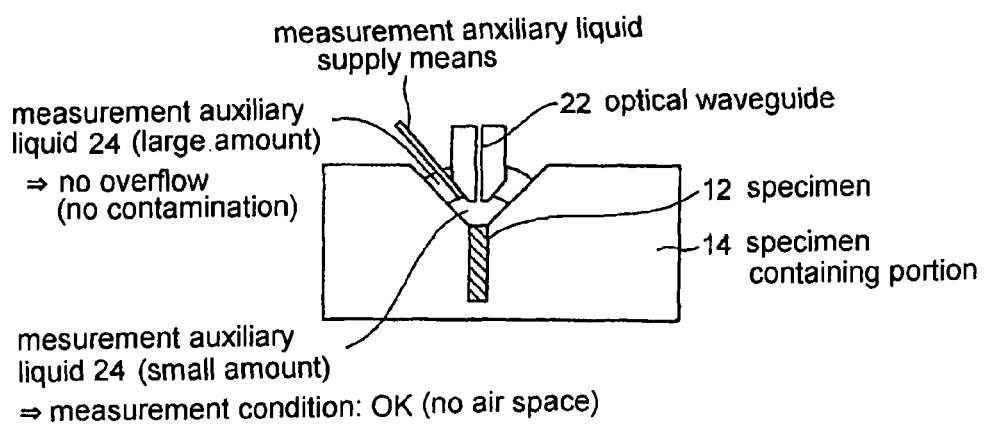

FIG. 10 is an explanatory diagram of a case in which the specimen containing portion has a cone shape opening.

FIG. 11 is a view showing an example of the specimen containing portion of the present invention.

FIG. 12 is a view showing an example of a fluid level control method of the present invention.

FIG. 13 is a cross-sectional view showing a relation among the measurement auxiliary liquid, the specimen, and the specimen containing portion.

FIG. 14 is a cross-sectional view showing another structure of the specimen containing portion.

Figure 15:
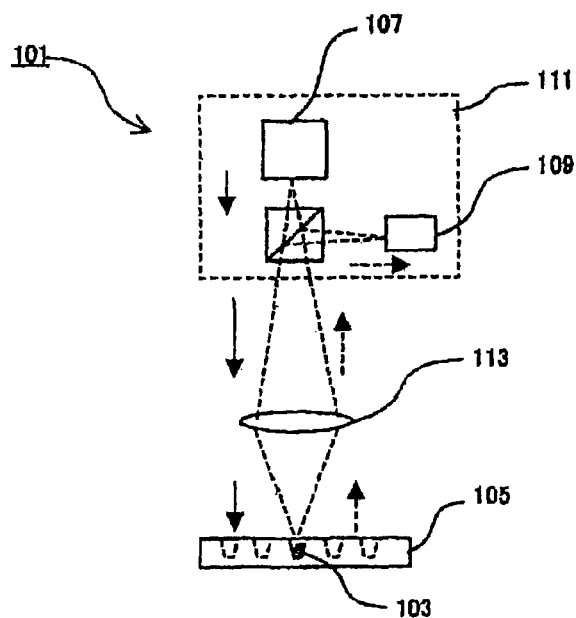

FIG. 15 is a schematic view showing a conventional apparatus for recognizing optical information from a specimen.

Figure 16:
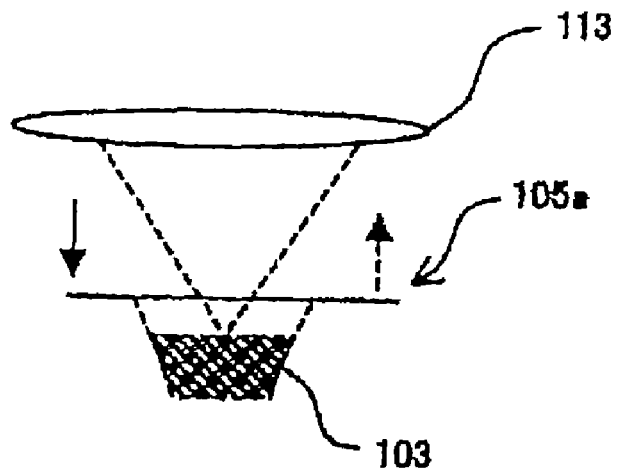

FIG. 16 is a schematic cross-sectional view showing a conventional specimen containing portion.

Figure 17:
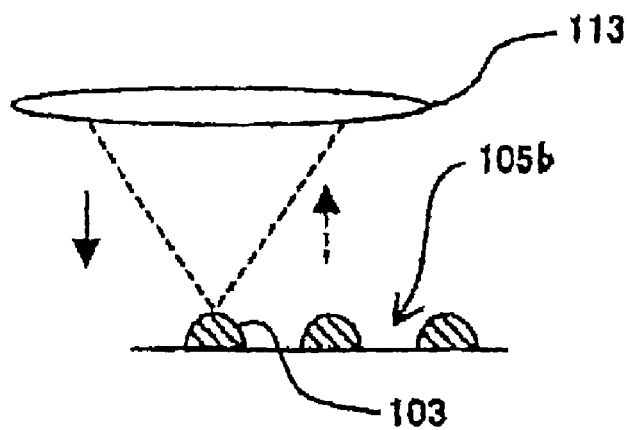

FIG. 17 is a schematic cross-sectional view showing another example of a conventional specimen containing portion.

EXPLANATION OF REFERENCE NUMERALS 10 apparatus for recognizing optical information from a specimen
12 specimen
14 specimen containing portion
16 photodetecting portion
18 light source
20 specimen measuring portion
22 optical waveguide
24 measurement auxiliary liquid

THE BEST MODE FOR CARRYING OUT THE CLAIMED INVENTION

Embodiments of the present invention will be described hereinafter in reference to the drawings. In the description of embodiments, the numerals are given to the same nominal components as those of the conventional examples shown in FIGS. 15 to 17, and the description thereof will be omitted to prevent a repeat of the description.

Figure 1A:
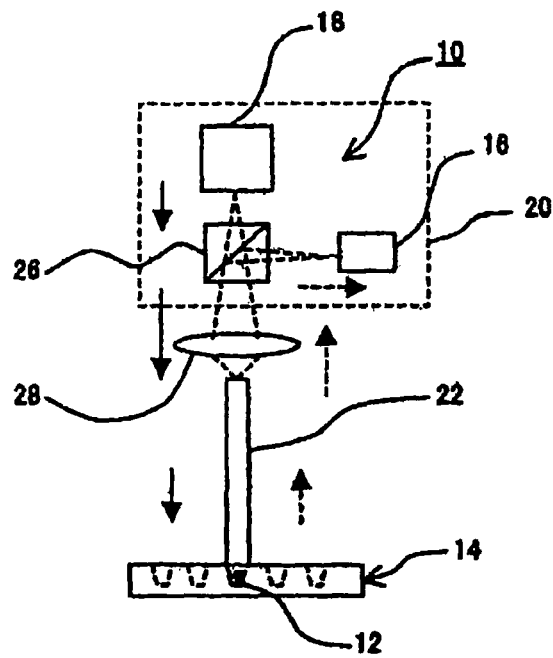
Figure 1B:
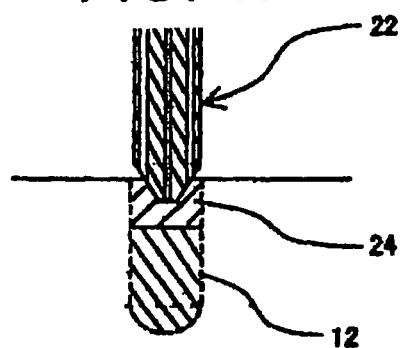
Figure 1C:
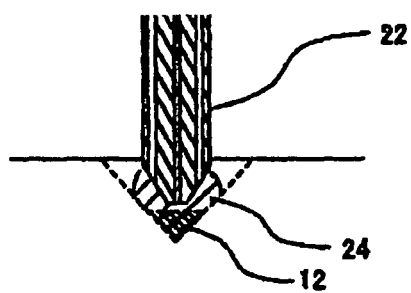

FIGS. 1A to 1C are views showing an embodiment of an apparatus 10 for recognizing optical information from a specimen according to the present invention. As shown in figures, the apparatus 10 for recognizing optical information of the embodiment comprises a specimen containing portion 14 for containing a specimen 12 to be measured, a specimen measuring portion 20 having a light source 18 for outputting light to observe the specimen 12 and a photodetecting portion 16 for collecting optical information from the specimen 12, and an optical waveguide 22 for transmitting light between the specimen containing portion 14 and the specimen measuring portion 20. A measurement auxiliary liquid 24 is interposed between the end of the optical waveguide and the specimen. Each part is particularly described thereinafter.

Figure 2A:
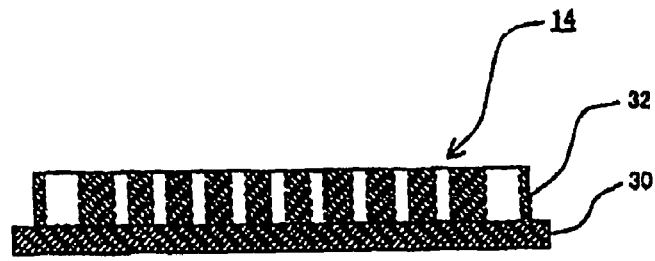
Figure 2B:
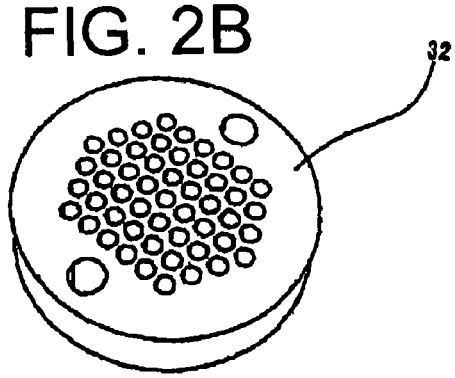

The specimen containing portion 14 can be typically prepared by cutting the metal, resin or glass, or by molding, furthermore applying a desired coating to the surface thereof as needed. Alternatively, as shown in FIG. 2A, the specimen containing portion 14 can be prepared by providing a sliced containing portion 32 having fine holes shown in FIG. 2B onto a base 30. The surface of the base 30 may be surface treated with a polymer to have hydrophilicity. Like the base 30, the inner walls of the fine holes of the sliced containing portion 32 may also be surface treated with a polymer to have hydrophilicity. The containing portion 32 may also be formed by using a sliced glass long body capable of transmitting the light such as an optical fiber.

If an optical fiber is used, portions other than the inner walls of the fine holes have hydrophobicity due to the characteristic of the material.

As described above, the inner walls of the fine holes on the containing portion 32 and the base 30 to be positioned at the bottom of the containing portion 32 can be surface treated with polymer to have hydrophilicity, making it possible to prevent the specimen from being attached and agglomerated to the internal surface of the specimen containing portion 14. Furthermore, the sliced face of the containing portion 32 has hydrophobicity due to the characteristic of material, making it possible to prevent the specimen from being mixed in fine holes for other samples.

Figure 2C:
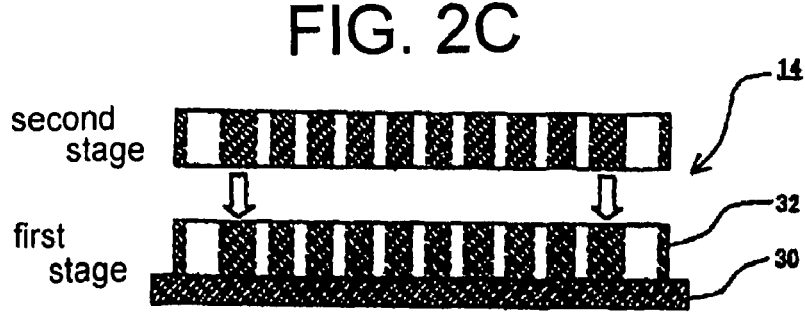
Figure 2D:
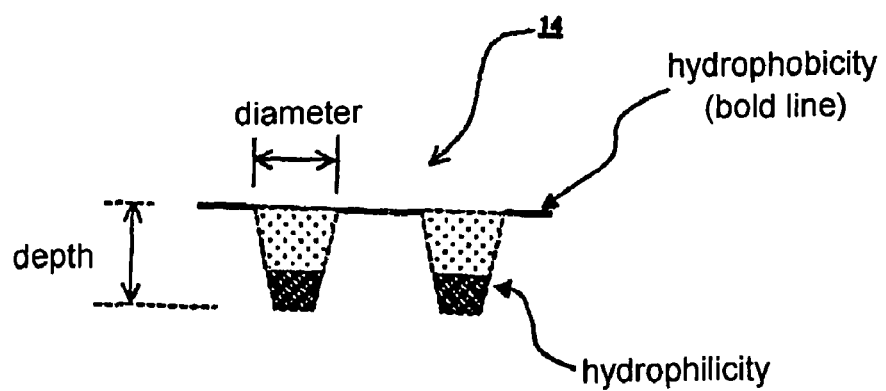

Moreover, the structure of the containing portion in the specimen containing portion 14 is formed in a well shape having a depth larger than an opening diameter thereof as shown in FIG. 2D. The opening diameter of the specimen containing portion 14 may be controlled by, for example, a design of the fine holes in the containing portion 32. The depth of the specimen containing portion 14 may be controlled by, for example, the number of the sliced containing portions 32 to be laminated as shown in FIG. 2C.

For example, when suspended solution such as peptide protein chip is measured, employment of the well shape having a depth larger than the opening diameter (diameter: 0.1 mm, depth: 0.3 mm) decreases a contact area with air so as to prevent evaporation of the solution and keeps reaction freedom of a sample so as to achieve a high efficiency reaction. In addition, the well shape makes it possible to increase a measurement capacity per unit measurement area in the measurement, and therefore a high sensitivity measurement can be performed.

FIG. 11 is a view showing an example of form of the specimen containing portion according to the present invention. A through hole for containing a specimen is provided at the bottom of an opening portion of a cone. Since the air can be released from the bottom portion, the specimen supplied from the top portion goes down by the own weight of the specimen into the hole as FIG. 11B and stops at approximately a certain position, therefore a fluid level can be controlled constant. The specimen positions in this case are approximately the same regardless how much amount of the specimen is supplied (see FIG. 11C).

FIG. 12 is an explanatory diagram for explaining the fluid level control method. As shown in FIG. 12, a cylinder structure is provided under the through hole, and the pressure can be changed. Therefore, the fluid level can be changed up and down. A light transmission type fluid level recognizing sensor is provided at the specimen containing portion formed of a transparent material. The fluid level can be exactly controlled by controlling the cylinder operation base on the information from this sensor. Alternatively, the fluid level information from the sensor may be used not as a feedback signal for controlling the fluid level but used as a signal for compensating the location of the optical waveguide. In either case, the exact analysis can be performed by controlling the distance between the tip of the optical waveguide and the fluid level of the specimen constant.

The specimen containing portion 14 may includes a functional thin film provided with a temperature controller and a vibrator, instead of the base 30. This is used to accelerate the reaction of the specimen when an amount of specimen sample is smaller. Generally, if an amount of a specimen sample is much, the reaction can be accelerated by agitation with pipetting. However, if an amount of a specimen sample is smaller, it is difficult to agitate with pipetting due to its quantity. In addition, contaminants may be mixed in other fine holes. By controlling the specimen temperature suitable for a specimen reaction, the specimen reaction is accelerated by the vibrator to enable reaction with high efficiency.

The above-mentioned specimen containing portion 14 can establish a manufacturing technology having advantageous with respect to stable product quality and cost. Moreover, using the functional thin film for the base 30 under the specimen containing portion 14 can achieve an optimal specimen reaction system based on temperature control and vibration.

Next, the specimen measuring portion 20 will be described.

The specimen measuring portion 20 includes the light source 18 for outputting light to measure the specimen 12 and the photodetecting portion 16 for collecting the optical information from the specimen 12. In FIG. 1A, a beam splitter 26 is provided. The beam splitter transmits the light from the light source 18 to the specimen 12 and achieves a 90-degree turn of the transmitting direction of the optical information collected from the specimen 12, without transmitting the optical information to the light source 18 to thereby transmit the optical information to the photodetecting portion 16. This beam splitter 26 may be provided according to needs. The turning angle of transmitting direction of the light information may be set arbitrary depending on the locations of the light source 18 and the photodetecting portion 16. Furthermore, if the optical waveguide 22 described hereinafter has a double core optical fiber structure, there is no necessity to use the beam splitter 26.

The optical waveguide 22 includes an optical fiber and a lens 28 for coupling the light output from the specimen measuring portion 20 with the optical fiber. The light output from the specimen measuring portion 20 is collected by lens 28 so as to be led to the optical fiber. The light led to the optical fiber is transmitted through the optical fiber and is emitted from a tip close to the specimen 12 of the optical fiber to the specimen 12 via measurement auxiliary liquid 24. Multiple optical fibers may be provided if necessary.

The installation structure and the number of the optical fiber are not particularly limited, but a bundle condition such as bundle fiber is preferred because it needs less space. Installation of multiple optical fibers enables the specimen to be measured in broader range. In addition, the optical information from the specimen can be obtained completely to achieve a high sensitivity measurement.

The measurement auxiliary liquid 24 is interposed between a surface close to the specimen 12 of the optical waveguide 22 and the specimen 12.

A refractive index of the measurement auxiliary liquid 24 is set to be equal to that of, for example, the core of the optical waveguide 22, therefore the loss due to Fersnel reflection can be eliminated. Furthermore, it is preferred that the measurement auxiliary liquid 24 is water-insoluble and has low volatile to prevent mixture of the measurement auxiliary liquid and the specimen and to prevent evaporation of the measurement auxiliary liquid. Silicone oil known as refractive index adjuster is suitable for the measurement auxiliary liquid 24. The measurement auxiliary liquid 24 is housed in the specimen containing portion 14 together with the specimen 12 for the purpose of protecting the specimen and supplementing the measurement. The measurement auxiliary liquid 24 is not limited to the above mentioned composition. In addition, the measurement auxiliary liquid 24 is preferably a liquid type, but may be a gel type.

The apparatus and method for recognizing optical information from the specimen 12 in which the measurement auxiliary liquid 24 is interposed will be described in detail below. As shown in FIGS. 3 and 4, an opening portion of the well of the specimen containing portion 14 is covered with droplet of the measurement auxiliary liquid 24, and measurement is performed under the condition that a core portion 22a of the optical waveguide 22 is in contact with the droplet. In the conventional fluorescent measurement of the specimen by the coupling through the air, there is a space, i.e. the air, between the specimen 12 and the optical measurement system (for example, the tip of the optical fiber), therefore the optical loss and noise are interfered with a high sensitivity measurement. In the measurement method according to the present embodiment, the core portion 22a of the optical waveguide 22 and the measurement auxiliary liquid 24 have the same refractive index, therefore the loss due to Fresnel reflection at the boundary surface of both is reduced to enable the sensitivity measurement. Since the specimen 12 is water solution, if aqueous measurement auxiliary liquid is used, it may be dissolved in the solution of the specimen 12, thereby unfavorably causing the change of dilution rate and contamination attachment at the tip of the optical the waveguide. The possibility of the contamination attachment can be avoided by using water-insoluble measurement auxiliary liquid according to application.

Use of the end face of the optical fiber for a measuring head in the optical waveguide 22 enables irradiation of a miniregion with the light and light reception, therefore a high sensitivity measurement can be achieved comparing to the conventional optical system using an objective lens. In a comparative experiment of the conventional and present systems using a plate reader, when the optical fiber was used, even 0.1 nL of an ultratrace amount of peptide reaction liquid sample could be measured.

Next, a light transmitting structure in the optical waveguide 22 and a supplying structure for supplying the measurement auxiliary liquid 24 and the specimen 12 will be described.

In order to achieve the measurement method of the specimen 12 by interposing the above-mentioned measurement auxiliary liquid 24, an optical fiber is used for the optical waveguide 22 as shown in FIGS. 4A and 4B. The optical fiber supplies the measurement auxiliary liquid 24 through its holes 23 for supplying droplet. Tip of the optical fiber is processed to be trapezoidal, thus droplets can be instantly formed at the core 22a. Since this droplet covers the measuring well (the specimen containing portion 14), the evaporation of the specimen 12 can be prevented. The shape of tip of the optical waveguide 22 is not limited to trapezoidal shape, so the shape of the tip of the optical waveguide 22 itself or of the optical waveguide 22 including adjacent members (e.g. ferule) to which the optical waveguide 22 is fixed may be cone-, pyramid-, or cuneiform-shaped. Specifically, when the cross section area of the optical waveguide perpendicular to the light transmitting direction is made smaller towards the tip of the optical waveguide 22, the tip of the optical waveguide 22 can be fittingly positioned in the specimen containing portion 14, resulting in a higher measurement accuracy.

FIGS. 3A to 3C are view showing an example of ways of supplying the measurement auxiliary liquid 24 and the specimen 12 and a measurement starting condition. First, as shown in FIG. 3A, the specimen 12 is injected into the specimen containing portion 14. Next, the measurement auxiliary liquid 24 is supplied though the holes 23 for supplying the measurement auxiliary liquid of the above-mentioned optical fiber to the tip of the optical fiber so as to form a droplet as shown in FIG. 3B. Then, as shown in FIG. 3C and FIG. 1B, the tip of the optical fiber is approached to the specimen so as to make the specimen come in contact with the measurement auxiliary liquid.

Since the specimen does not adhere to the tip of the optical fiber after the measurement, when the tip of the optical fiber leaves from the well, it can prevent contaminants from being mixed in other wells.

Ways of supplying the measurement auxiliary liquid 24 and the specimen 12 other than the above-mentioned steps may be employed. For example, a method in which the optical fiber is approached to the measurement auxiliary liquid 24 after supplying the measurement auxiliary liquid 24 onto the contained specimen 12, or a method in which the optical fiber is approached to the specimen 12 to supply the measurement auxiliary liquid 24 into a gap therebetween may be employed.

The specimen is measured at only one location in the above-mentioned embodiment, but the specimen may also be measured by moving the tip of the optical waveguide to locations with different distances from the specimen and angles to the specimen. In other words, this structure is capable of scanning the specimen at multiple locations. For example, when one specimen is measured by moving the optical waveguide, the first measurement may be performed with the tip of the optical waveguide being positioned in the measurement auxiliary liquid, and the second measurement may be performed with the tip of the optical waveguide being moved to the upper direction of FIGS. 3A to 3C without positioning in the measurement auxiliary liquid. The specimen optical information can be recognized from these two measurement results. The number of the measurement is not limited to two as described above, but may be selected appropriately.

In the above-mentioned embodiment, the measurement at multiple locations by moving the optical waveguide was described, but the measurement may also be performed by changing the measurement conditions such as wavelength or light intensity to be obtained from specimen without moving the optical waveguide. In this case, control of the light source and the photodetecting portion enables the measurement. In this manner, the specimen optical information can be recognized based on the measured values measured under at least two measurement conditions, thus the measurement of the specimen with a higher sensitivity can be performed.

For a plane scan in the well (specimen containing portion 14) for measuring a single cell which is a miniregion, an ultramicro square spindle wedge fiber head (diameter is 6 μm) as shown in FIG. 5 may be used, thereby attaining extremely lighter structure because the fiber is the only element to be moved. As a result, the plane scan within the well for measuring a single cell which is a miniregion can be performed.

FIGS. 13A and 13B are cross-sectional views showing a relationship among the measurement auxiliary liquid, the specimen, and the specimen containing portion. As shown in FIG. 13A, a through hole is provided in the center of the specimen containing portion 14. In the case of FIG. 13A, the measurement auxiliary liquid 24 is arranged above and below the specimen 12. The measurement auxiliary liquids 24 positioned above and below the specimen 12 may be of identical liquids, or of different liquids. For example, when different liquids are used, liquids with different densities are injected in turn. When the identical liquids are used, a liquid is supplied to the cone portion of the specimen containing portion and then is sucked. In the case of FIG. 13B, the measurement auxiliary liquid 24 is arranged only above the specimen 12.

Figure 14A:
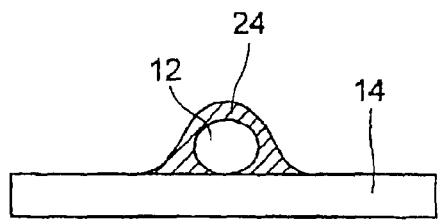
Figure 14B:
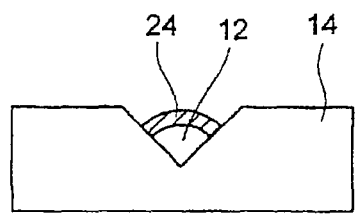
Figure 14C:
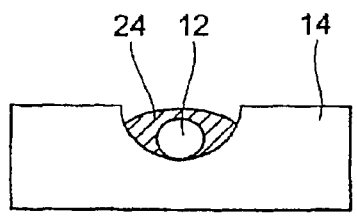

FIGS. 14A to 14C are cross-sectional views showing another structure of the specimen containing portion. In the case of FIG. 14A, the specimen 12 is arranged on a flat upper surface of the specimen containing portion 14, and the measurement auxiliary liquid 24 is arranged so as to cover the specimen entirely. In the case of FIG. 14B, a specimen containing portion 24 has a wedge-shaped portion shown in section on the upper surface thereof. In this case, the specimen 12 is arranged in the wedge-shaped portion, and the measurement auxiliary liquid 24 is arranged so as to cover the specimen entirely. In the case of FIG. 14C, a specimen containing portion 14 has a semicircle portion shown in section on the upper surface thereof. In this case, the specimen 12 is arranged in the semicircle portion, and the measurement auxiliary liquid 24 is arranged so as to cover the specimen entirely. As shown in FIGS. 14A to 14C, a specimen may be arranged in accordance with the shapes of the specimen containing portions.

Next, a specimen measuring system 50 using the above-mentioned device for recognizing optical information from a specimen will be described.

FIGS. 6 to 9 are views showing the specimen measuring system 50 which utilizes the device and method for recognizing optical information from a specimen shown in FIGS. 1 to 5 as described above. The reaction of a specimen with a reagent is conducted in the specimen measuring system 50. This measuring system 50 includes a measuring unit 52, an information obtaining unit 54, and a controlling/analyzing device 56 as shown in FIG. 6. In this embodiment, a fully automatic system is demonstrated. Automation of each process provides quantification of the measurement and prevention of contamination interfusion. The reaction and the measuring operation will be outlined below.

As shown in FIG. 7, panels of the measuring unit 52 includes a three-dimensional rotating head 58, a reaction substrate 60, a sample/reagent tank 62, a cleaning tank 64, and a drying tank 66. The head 58 has pipettes 68 for collecting minute sample and wedge fiber measuring portions 70. As shown in FIG. 7 and FIG. 9, the head 58 is capable of moving and rotating in accordance with each process. A sample (specimen) to be measured and a peptide library are accommodated in the sample/reagent tank 62. The three-dimensional rotating head 58 moves and rotates so that, first of all, a tip of the pipette 68 is cleaned and dried, then the pipette 68 obtains a predetermined library and dispenses the same into predetermined wells of the reaction substrate 60.

Thereafter, the tip of the pipette 68 is cleaned and dried, and then the pipette 68 obtains a sample and dispenses the same into the wells of the reaction substrate 60 in which the library was dispensed. In each well, the sample reaction is carried out under the optimized condition by using a temperature controller or a vibrator (not shown). The three-dimensional rotating head 58 rotates, so that the tip of the wedge fiber measuring portion 70 supplies the measurement auxiliary liquid to the wells to seal the wells with the measurement auxiliary liquid. This provides the prevention of the solution evaporation and the stabilization of the optimal condition of the reaction. The number of axes per one tool can be reduced by employing rotational operation. This easily enables the reductions in weight and size of the operable portion. A precise positioning structure which has less back lash can be easily achieved as well. FIG. 8 shows a measurement stand-by state or a state where a successive observation has been started. At this time, the tip of the wedge fiber measuring portion 70 comes into contact with the measurement auxiliary liquid. The measurement is continued until the reaction is completed. After measuring, the head 58 ascents and the whole process is executed by repeating the reaction and the measurement. When a minute sample such as a single cell is measured, the wedge fiber measuring portion 70 may be scanned within the well under the condition that the minute sample is sealed with the measurement auxiliary liquid, thereby obtaining the maximum value.

As described above, the system 50 is the fully automatic reacting/measuring system capable of preventing the solution from being evaporated and stabilizing the optimal condition of the reaction condition, and achieving the high measurement sensitivity of minute sample with a high efficiency reaction substrate and the measuring method.

If fluorochromes to be measured are different depending on application, this system is applicable to multicolor by preparing wedge fiber heads for each fluorochrome. In addition, a high sensitivity measurement can be achieved by irradiating the specimen with the exciting light having an optimal characteristic for the fluorochrome of the specimen.

The above-mentioned system is applicable not only to the peptide protein analysis and the single cell ligand screening to be measured, but also broadly-applicable to various uses using only one system. Examples of the uses may be includes a real-time analysis of a stem cell differentiation process, an analysis of a high specification SNPs, a real-time dynamic state analysis of a cell due to medication effect, and a high sensitivity measurement of a cell and protein with nano-fluorescent. Accordingly, the system has an advantageous of high versatility.

The invention claimed is:

1. An apparatus for recognizing optical information from a specimen, comprising:
   a specimen containing portion configured to contain a specimen to be measured;
   a specimen measuring portion including a photodetecting portion configured to collect optical information from the specimen; and
   an optical waveguide configured to transmit a light between the specimen containing portion and the specimen measuring portion, the optical waveguide including an optical fiber, wherein,
   a measurement auxiliary liquid is interposed between a tip of the optical fiber and the specimen, the auxiliary liquid being in contact with the specimen, and
   the optical information from the specimen is recognized based on measurement values measured under two or more measurement conditions.

2. An apparatus for recognizing optical information from a specimen, comprising:
- a specimen containing portion for containing a specimen to be measured;
- a specimen measuring portion having a photodetecting portion for collecting optical information from the specimen;
- an optical waveguide including an optical fiber for transmitting a light between the specimen containing portion and the specimen measuring portion; and
- a measurement auxiliary liquid interposed between a tip of said optical waveguide and the specimen, the auxiliary liquid being in contact with the specimen.

3. The apparatus for recognizing optical information from a specimen according to claim 1,
wherein the specimen measuring portion further comprises a light source for outputting a light for observing the specimen.

4. The apparatus for recognizing optical information from a specimen according to claim 2,
wherein the specimen containing portion is formed in a planer shape or a shape having a concave portion so that the specimen to be measured is positioned by its weight, and
the specimen containing portion has a surface having a lower affinity for the specimen than that for the measurement auxiliary liquid.

5. The apparatus for recognizing optical information from a specimen according to claim 1, wherein
the specimen containing portion has a concave portion in vertical cross-section, and
an opening depth of the concave portion is equal to or larger than the opening diameter.

6. The apparatus for recognizing optical information from a specimen according to claim 1,
wherein the specimen containing portion is provided with a through hole at a bottom of the specimen containing portion.

7. The apparatus for recognizing optical information from a specimen according to claim 6,
wherein the through hole has a uniform opening diameter in the depth direction or a different opening diameters in the depth direction to be a stepped hole shape.

8. The apparatus for recognizing optical information from a specimen according to claim 1,
wherein the specimen containing portion is configured such that an opening portion thereof is conical or polyhedral in shape with an oblique angle of 10 degree or more and a bottom portion thereof is provided with a recessed portion for finally housing the specimen.

9. The apparatus for recognizing optical information from a specimen according to claim 6,
wherein the specimen containing portion has a function portion having a function to change a containing position of the specimen by changing a pressure in a space below the specimen.

10. The apparatus for recognizing optical information from a specimen according to claim 1,
wherein the specimen containing portion comprises a functional portion having a sensing function to recognize a fluid level of the specimen.

11. The apparatus for recognizing optical information from the specimen according to claim 6, wherein the specimen containing portion comprises:
- a functional portion having a function to change a containing position of the specimen by changing a pressure in a space below the specimen; and
- a functional portion having a sensing function to recognize a fluid level of the specimen so as to be capable of controlling the fluid level of the specimen.

12. The apparatus for recognizing optical information from a specimen according to claim 1,
wherein the specimen containing portion comprises a temperature controller for controlling a temperature of the specimen.

13. The apparatus for recognizing optical information from a specimen according to claim 1,
wherein the specimen containing portion comprises a vibrator for vibrating the specimen.

14. The apparatus for recognizing optical information from a specimen according to claim 1,
wherein the specimen containing portion comprises a containing portion provided with a fine through hole and a base which closes the fine through hole, the containing portion and the base being formed as separate parts.

15. The apparatus for recognizing optical information from a specimen according to claim 1, further comprising:
a supplying unit for supplying a composition other than the specimen to be measured to the specimen containing portion or the tip of the optical waveguide.

16. The apparatus for recognizing optical information from a specimen according to claim 15,
wherein the optical fiber is provided with an inlet and an outlet for allowing through-flow of one of the specimen to be measured and the composition other than the specimen.

17. The apparatus for recognizing optical information from a specimen according to claim 1,
wherein the tip of the optical waveguide or of the optical waveguide including an adjacent member to which the optical waveguide is fixed is cone-, pyramid-, or wedge-shaped.

18. The apparatus for recognizing optical information from a specimen according to claim 15,
wherein the composition other than the specimen is water-insoluble.

19. The apparatus for recognizing optical information from a specimen according to claim 15,
wherein the composition other than the specimen has a refractive index equal to that of the optical waveguide or the specimen, or equal to a refractive index having a value between the refractive index of the optical waveguide and the refractive index of the specimen.

20. The apparatus for recognizing optical information from a specimen according to claim 1,
wherein there is no space at least in a light path between the tip of the optical waveguide and the specimen.

21. A method for recognizing optical information from a specimen, comprising:
- housing a specimen to be measured in a specimen containing section;
- collecting optical information from the specimen via an optical waveguide including an optical fiber under two or more measurement conditions;
- interposing a measurement auxiliary liquid between a tip of the optical fiber and the specimen, the auxiliary liquid being in contact with the specimen; and
- analyzing the specimen based on the collected optical information.

22. The method for recognizing optical information from a specimen according to claim 21,
wherein the two or more measurement conditions are that the optical information from the specimen are collected at two or more different locations.

23. A method for recognizing optical information from a specimen, comprising:
- housing a specimen to be measured in a specimen containing portion;
- transmitting optical information from the specimen to a tip of a waveguide including an optical fiber, by way of a measurement auxiliary liquid interposed between a tip of the optical fiber and the specimen, the auxiliary liquid being in contact with the specimen, so as to collect the optical information from the specimen;
- analyzing the specimen based on the collected optical information.

24. A method for recognizing optical information from a specimen, comprising:
- housing a specimen to be measured in a specimen containing portion;
- transmitting a first optical information from the specimen through air so as to collect the first optical information and transmitting a second optical information from the specimen through an optical fiber, by way of a measurement auxiliary liquid interposed between a tip of the optical fiber and the specimen, the auxiliary liquid being in contact with the specimen, so as to collect the second optical information; and
- analyzing the specimen based on the first and second optical information.

25. The method for recognizing optical information from a specimen according to claim 21, further comprising:
- irradiating the specimen with a light to allow the specimen to output the optical information.

26. The method for recognizing optical information from a specimen according to claim 21, further comprising:
- scanning the specimen with a tip of the optical waveguide so as to collect a plurality of optical information from the specimen; and
- analyzing the specimen based on the plurality of optical information.

27. A specimen measuring system comprising:
- the apparatus for recognizing optical information from a specimen according to claim 1;
- a measuring unit for operating the apparatus for recognizing optical information from a specimen and for collecting an information on the specimen; and
- a controlling and analyzing device for analyzing the information from the measuring unit and for controlling the apparatus for recognizing optical information from a specimen.

28. The specimen measuring system according to claim 27, further comprising:
- a total of more than two components including a specimen supplying unit for supplying a specimen to the specimen containing portion and an optical waveguide for collecting optical information, wherein,
- the more than two components are fixed to a fixing member capable of moving and rotating, and
- the component necessary for measurement of the specimen is properly selected from among the more than two components by rotation and movement of the fixing member.

29. The apparatus for recognizing optical information according to claim 1, further comprising:
- a specimen supplying unit for supplying a specimen to the specimen containing portion.

* * * * *

UNITED STATES PATENT AND TRADEMARK OFFICE
CERTIFICATE OF CORRECTION

| | | |
|---|---|---|
| PATENT NO. | : 7,999,929 B2 | Page 1 of 1 |
| APPLICATION NO. | : 11/659132 | |
| DATED | : August 16, 2011 | |
| INVENTOR(S) | : Ken Tsukii et al. | |

It is certified that error appears in the above-identified patent and that said Letters Patent is hereby corrected as shown below:

On the title page, Item (86), the Application Filing Date is incorrect. Item (86) should read:

-- (86) PCTNo.:  PCT/JP2005/014057

§371 (c)(1),
(2), (4) Date: Apr. 19, 2007 --

Signed and Sealed this
Eighteenth Day of October, 2011

David J. Kappos
*Director of the United States Patent and Trademark Office*